(12) United States Patent
Dycher et al.

(10) Patent No.: US 11,534,520 B2
(45) Date of Patent: Dec. 27, 2022

(54) WICKING DEVICE FOR EVAPORATING FRAGRANCE HAVING A FLOW CHANNEL

(71) Applicant: CTR, LDA, Samora Correia (PT)

(72) Inventors: David Dycher, Isle of Man (GB); Pedro Queiroz Vieira, Belas (PT)

(73) Assignee: CTR, LDA, Samora Correira (PT)

( * ) Notice: Subject to any disclaimer, the term of this patent is extended or adjusted under 35 U.S.C. 154(b) by 1045 days.

(21) Appl. No.: 16/310,264

(22) PCT Filed: Jun. 16, 2016

(86) PCT No.: PCT/EP2016/001006
§ 371 (c)(1),
(2) Date: Dec. 14, 2018

(87) PCT Pub. No.: WO2017/215726
PCT Pub. Date: Dec. 21, 2017

(65) Prior Publication Data
US 2019/0117818 A1    Apr. 25, 2019

(51) Int. Cl.
*A61L 9/03*    (2006.01)
*A01M 1/20*    (2006.01)

(52) U.S. Cl.
CPC ............ *A61L 9/037* (2013.01); *A01M 1/2044* (2013.01); *A01M 1/2077* (2013.01); *A61L 2209/133* (2013.01)

(58) Field of Classification Search
CPC ............... A01M 1/2044; A01M 1/2077; A61L 2209/133; A61L 9/037
USPC ....... 392/391, 386, 390, 392, 394, 395, 405, 392/406; 122/366, 367.1, 367.2; 43/129, 43/130; 219/543, 544; 239/44, 45, 58, 239/202; 261/26, 30, 101, DIG. 88
See application file for complete search history.

(56) References Cited

U.S. PATENT DOCUMENTS 3,793,763 A * 2/1974 Griffin ................ A01M 1/2077
43/129
5,015,442 A    5/1991 Hirai
(Continued)

FOREIGN PATENT DOCUMENTS

CN    1993043 A    7/2007
DE    202005015709 U1    12/2005
(Continued)

*Primary Examiner* — Helena Kosanovic
*Assistant Examiner* — Ket D Dang
(74) *Attorney, Agent, or Firm* — Laurence A. Greenberg; Werner H. Stemer; Ralph E. Locher (57) ABSTRACT

A device has a container for a substance to be dispensed. A wick as a capillary element in contact with the substance in the container and forms part of the container. The wick has a wick-side substance dispensing area. A heating element produces a substance air flow, which is enriched with substance and flows away from the device, by heating the wick-side substance dispensing area and a substantially substance-free hot air flow that flows away from the device and is warmer than the substance air flow, by heating the air surrounding the heating element. A flow-guiding and/or deflecting apparatus guides and/or deflects at least one of the air flows, preferably the substance-free hot air flow, such that the air flows hit each other, preferably at a defined angle of incidence, and form a common substance-and-hot-air flow flowing away from the device.

35 Claims, 6 Drawing Sheets

(56) References Cited

U.S. PATENT DOCUMENTS

| | | | | |
|---|---|---|---|---|
| 6,325,475 B1 * | 12/2001 | Hayes | ...................... | A61B 5/00 |
| | | | | 128/203.11 |
| 6,563,091 B2 | 5/2003 | Vieira | | |
| 6,968,124 B1 * | 11/2005 | Varanasi | ............. | A01M 1/2077 |
| | | | | 392/395 |
| 7,167,641 B2 | 1/2007 | Tam et al. | | |
| 2008/0226269 A1 | 9/2008 | DeWitt et al. | | |
| 2010/0021855 A1 | 1/2010 | Requejo et al. | | |
| 2017/0108210 A1 * | 4/2017 | Meinhart | ................... | F22B 1/30 |
| 2017/0303523 A1 * | 10/2017 | Sandford | .............. | A01M 1/023 |

FOREIGN PATENT DOCUMENTS

| | | | | | |
|---|---|---|---|---|---|
| EP | | 1247447 | A1 | 10/2002 | |
| WO | | 9858692 | A1 | 12/1998 | |
| WO | | 0121226 | A1 | 3/2001 | |
| WO | | 2006002404 | A1 | 1/2006 | |
| WO | | 2006052519 | A2 | 5/2006 | |
| WO | | 2006105396 | A1 | 10/2006 | |
| WO | | 2006130410 | A2 | 12/2006 | |
| WO | | 2009006582 | A1 | 1/2009 | |
| WO | | 2009085170 | A1 | 7/2009 | |
| WO | WO-2009085170 | A1 * | 7/2009 | ............... | A61L 9/02 |

* cited by examiner

– 1 –
WICKING DEVICE FOR EVAPORATING FRAGRANCE HAVING A FLOW CHANNEL

BACKGROUND OF THE INVENTION

Field of the Invention

The invention relates to a device and a method for dispensing, in particular for vaporizing, volatile substances, in particular fragrances and/or active agents. The device has a container for the substance to be dispensed. A wick as a capillary element which is in contact with the substance to be dispensed, is arranged at least in regions in the container, forms a constituent part of the container and comprises a wick-side substance dispensing region. In addition, the invention relates to a method for dispensing, in particular for vaporizing, volatile substances, in particular fragrances and/or active agents.

Devices for dispensing, in particular for vaporizing, volatile substances, in particular fragrances and/or active agents, are known generally and as a rule include a container in which a substance to be dispensed is received. A wick, which projects beyond the container by way of a free wick end and is in contact with the substance to be dispensed in such a manner that said substance is conveyed in the direction of the free wick end by means of the capillary action of the wick, is arranged in the container as a capillary element. A heating element, in particular an electrical heating element, is regularly assigned to the free wick end, by means of which the free wick end is able to be acted upon with heat in order to be able to dispense or vaporize the substance accumulating in the free wick end even quicker to the surrounding area. Such a design is disclosed, for example, in WO 98/58692 A1. In order to be able to adjust the degree of vaporization and consequently the vaporization performance, said WO 98/58692 A1 further provides mounting the container together with the wick so as to be vertically adjustable in the housing of the device such that the relative position of the wick is modifiable with respect to the heating device.

With such a design, it is possible to influence the vaporization rate and consequently the dispensing rate of the substance to be dispensed over a longer period. In the case of such devices, however, the problem regularly arises that the substance air stream, which is generated and enriched with the substance to be dispensed and escapes into the surrounding area via an outlet opening in the housing wall, is influenced by air turbulence created in the interior of the housing such that, on the one hand, the flowing away of the substance air stream is impaired and that, on the other hand, unwanted deposits and condensation of the substance to be dispensed occur to a certain extent on the inside walls of the housing. The air vortices or turbulence in the housing interior are brought about, in particular, as a result of rising hot air which is generated, in turn, by the emission of heat from the electrical heating element to the air surrounding the heating element.

SUMMARY OF THE INVENTION

Accordingly, it is the object of the present invention to create a device and a method for dispensing, in particular for vaporizing, volatile substances, in particular fragrances and/or active agents, by means of which device or method the substance dispensing can be designed in a more effective manner or the efficiency of the substance dispensing can be increased even further.

Said object is achieved with the features of the independent patent claims. Advantageous designs in this respect are the object of the subclaims which are dependent thereon.

There is provided a device for dispensing, in particular for vaporizing, volatile substances, in particular fragrances and/or active agents, having a container for the substance to be dispensed and having a wick as a capillary element which is in contact with the substance to be dispensed, is arranged in the container at least in regions, forms a constituent part of the container and comprises a wick-side substance dispensing region. Provided according to the invention is at least one heating element, by means of which a substance air stream, which is enriched with substance and flows away from the device, is generatable as a result of heat emission to the wick-side substance dispensing region and by means of which a separate hot air stream which is substantially substance-free, flows away from the device and is preferably warmer than the substance air stream, is generatable as a result of heat emission to the air surrounding the at least one heating element. Further provided is at least one flow-guiding and/or deflecting device, by means of which at least one of the air streams flowing out, preferably the substance-free hot air flow, is guidable and/or deflectable such that the two air streams flowing away from the device meet one another preferably at a defined angle of incidence and realize one common substance hot air stream which flows away from the device.

With the solution according to the invention, a separate hot air stream generated by heat emission to the air surrounding the heating element is consequently used in a targeted manner for the purpose of entraining a substance air stream, which, in turn, enables considerably better distribution in space of the substance dispensed by the device. In this case, the fact that the hot air stream regularly comprises a considerably higher temperature and consequently also a considerably higher flow speed than the, in comparison, cooler substance air stream which is enriched with the substance to be dispensed, is able to be utilized in an advantageous manner.

By a controlled, directed hot air stream now being generated with the hot air that occurs regularly in any case in the device, the hot air occurring in or on the device cannot result in any unwanted turbulence or eddying in or on the device so that the substance air stream is able to flow away unimpeded and, in addition, the risk of condensation of substance to be dispensed in or on the device, for example on the housing walls of the device, is clearly reduced.

In addition, with the solution according to the invention, for example in conjunction with devices that can be arranged on walls or wall-side outlets, it is possible to ensure in a simple manner that the substance air stream, which is cooler than the hot air stream, is reliably kept away from a wall adjoining the device or can be steered away from the same. In particular, this also produces very good, unimpeded distribution of the substance in space.

With the solution according to the invention, the substance dispensing can consequently be designed more effectively or the efficiency of the substance dispensing can be increased even more.

The term "substance to be dispensed" is to be understood here specifically in a broad sense and includes all substances which can be conveyed by means of the capillary action of a wick as a capillary element. Along with volatile substances, these can also be specifically gel-like or other suitable substances. The term "wick" is also to be understood here in a comprehensive sense and specifically includes any capillary element which is suitable to convey a substance by means of capillary action.

Particularly preferred in this connection is a specific design of a device for dispensing, in particular for vaporizing, volatile substances, in particular fragrances and/or active agents, which comprises a housing with at least one housing wall. In addition, the device comprises a container in which a substance to be dispensed is received. The device additionally comprises a wick as a capillary element which is in contact with the substance to be dispensed, is arranged at least in regions in the container, forms a constituent part of the container and comprises a wick-side substance dispensing region which is assigned to a substance outlet opening region realized in the housing wall. The device further comprises at least one heating element, preferably at least one electrical heating element, by means of which a substance air stream, which is enriched with substance and flows away from the device via the substance outlet opening region (and consequently through the housing wall), is generatable as a result of heat emission to the wick-side substance dispensing region. In addition, at least one further outlet opening region is realized in the housing wall as a hot air outlet opening region, via which the separate hot air stream, which is generated by the at least one heating element as a result of heat emission to the air surrounding the at least one heating element and is substantially substance-free, flows away from the device through the housing wall. In addition, at least one flow-guiding and/or deflecting device is provided, by means of which at least one of the air streams flowing out, preferably, however, the substance-free hot air flow, is guidable and/or deflectable such that the two air streams flowing away from the device meet one another preferably at a defined angle of incidence and realize one common substance hot air stream which flows away from the device, the separate air streams flowing away from the substance outlet opening region and from the hot air outlet opening region meeting one another in a region outside the housing and realizing the common substance hot air stream which flows away from the device.

The hot air outlet opening region, in this case, can be realized adjacent to and/or adjoining the substance outlet opening region, which specifically includes any arrangement possibility, that is to say, for example, includes such an adjacent or adjoining realization and arrangement where the two outlet opening regions, without separation of the same, directly adjoin one another, for example, by means of a wall region or a partition element and, for example, are a constituent part of one and the same recess in the housing wall. Or as an alternative to this, the outlet opening regions, however, can also be separated by any component or a wall region and as a result be spaced apart from one another, that is to say, for example, be formed by two openings which are separated from one another by a wall region. The terms hot air outlet opening region and substance outlet opening region are consequently simply to express that there is a region of some type, through which the one air stream flows, and a region of some type through which the other air stream flows prior to their meeting.

Even if not explicitly named here, it is clear that obviously more than one substance air stream and/or more than one hot air stream could be present, for example in such a manner that multiple separate hot air streams meet one substance air stream or, where applicable, also one of multiple substance air streams.

According to a particularly preferred design according to the invention, it is provided that the flow-guiding and/or deflecting device comprises at least one flow-guiding element which is assigned to the substance air stream and/or to the substance outlet opening region and/or at least one flow-guiding element which is assigned to the hot air outlet opening region, by means of which an air stream flowing away from the device is guidable or steerable in a particularly functionally-reliable manner in the direction of the other air stream. Particularly preferred in said context is a design where the flow-guiding and/or deflecting device comprises at least one flow-guiding element which is assigned only to the hot air outlet opening region, by means of which the hot air stream flowing away from the hot air outlet opening region is deflectable in the direction of the substance air stream. The preferred deflection of only the hot air stream comprises the advantage of said hot air stream being especially suitable to influence the outflow behavior and the characteristics of the common substance hot air stream which joins the two air streams, for example relating to the realization of eddying and/or of turbulence at a certain outflow height above the meeting point of the two streams or above the device. In addition, by the hot air stream, as shown previously, regularly comprising a higher temperature and consequently a higher speed, particularly advantageous deflecting of the substance air stream away from components, such as, for example a wall, can be achieved.

In principle, there is a wide variety of design possibilities for the housing or the housing wall in which the substance outlet opening region and the hot air outlet opening region are arranged located side by side or adjoining one another. According to a particularly simple solution which is advantageous as regards manufacturing, it is proposed that the substance outlet opening region and the hot air outlet opening region lie side by side spaced apart in one plane, preferably in such a manner that the housing wall, at least on or in a housing wall region comprising the substance outlet opening region and the hot air outlet opening region, is realized in a planar and/or plate-shaped manner. As an alternative to this, according to a particularly preferred design, the substance outlet opening region and the hot air outlet opening region, when viewed in the direction of the vertical axis, can lie side by side spaced apart at different height planes. This makes it possible in a particularly simple manner to establish when and how the streams meet one another. This is true in particular when the hot air outlet opening region, when viewed in the direction of the vertical axis, lies above the substance outlet opening region. In order to realize this, it can be provided, for example, that the housing wall is realized in a stepped manner or comprises a stepped wall region. The substance outlet opening region can then be arranged in the region of a first step and the hot air outlet opening region in the region of a second or a further step.

Particularly advantageous, in addition, is a design where the substance air stream flowing away from the substance outlet opening region is an air stream which is not influenced by any flow-guiding element and is consequently uninfluenced and preferably flows in a substantially rectilinear manner away from the substance outlet opening region. In such a case, the hot air outlet opening region has associated therewith at least one flow-guiding element of the flow-guiding and/or deflecting device, by means of which the hot air stream flowing away from the hot air stream outlet opening region is deflectable in such a manner that the hot air stream meets the substance air stream at an angle or at a defined angle of incidence. Excellent outflow results are produced, in particular, with such a solution with the substance to be dispensed being distributed in space in an advantageous manner.

According to a first realization variant, the substance outlet opening region can be formed, for example, in a simple manner simply by a housing wall-side outlet opening (whilst the hot air outlet opening region, in this case, is then also formed by a separate opening which can then be once again, for example, a constituent part of a flow channel, as will be described in more detail below). Said housing wall-side outlet opening can be formed, for example, by an outlet opening which broadens outwardly in a funnel-shaped manner in the direction of flow, preferably broadens with a convex curvature, which has proven particularly advantageous when the substance air stream flowing away from or flowing out of the outlet opening is deflected by the hot air stream meeting it, because no unwanted flow stalls can occur at the edges of the outlet opening and consequently no eddying and turbulence. As an alternative to this, however, the substance outlet opening region can also be a constituent part of a housing wall-side recess, which also realizes or realizes in shared manner the hot air outlet opening region, that is to say, for example, directly adjoin one another. In such a case, it can then be provided, for example, that the recess region realizing the substance outlet opening region is upwardly tapered at least in regions, when seen in the direction of flow of the substance air stream, in order also to obtain functionally reliable diverting of the air stream enriched with substance.

According to a particularly preferred specific design, the flow-guiding element is aligned in the direction of the other air stream, preferably in an angled and/or curved manner, that is to say, for example, a flow-guiding element which is assigned to the hot air outlet opening region, is aligned in the direction of the substance air stream, for example in an angled and/or curved manner, such that the hot air stream is then able to meet the substance air stream at a defined angle.

The flow-guiding element is realized in a preferred manner such that it extends from the substance outlet opening region and/or the hot air outlet opening region, preferably from the hot air outlet opening region, away to the outside, away from the housing wall.

According to a particularly preferred further development, the flow-guiding element can be formed, for example, in the simplest means by a guide vane. As an alternative to this, however, the flow-guiding element can also be formed by a preferably angled and/or curved flow shaft or flow channel which, when seen in the direction of flow, extends away from an inflow opening and is aligned in the direction of the other air stream, wherein at its end opposite the inflow opening, the flow shaft or flow channel comprises an outflow opening which points in the direction of the other air stream. Such a flow shaft or flow channel is simple to produce and enables particularly advantageous and functionally reliable deflection of the respective air stream, in particular of the hot air stream in the direction of the other air stream. For example, such a flow shaft or flow channel can be formed by an angled or curved channel-like flow hood which projects in the manner of a dome or in a raised manner from the housing wall or is fitted there. Such an angled or curved flow shaft or flow channel can be formed specifically, for example, by an angled or curved channel-like flow hood which comprises two oppositely situated, substantially plate-like hood walls, between which is arranged an angled or curved wall region which brings about the deflection of the air stream. In a preferred manner, the inflow opening, in this case, is realized in the housing wall itself.

The terms "angled or curved" is always to be understood in the present case in a broad sense and is to include any realizations by way of which an air stream can be deflected, that is to say explicitly also a flow-guiding element which is set at an angle, to name but one example.

As the statements made previously show, the flow-guiding element can consequently be realized according to a particularly preferred design such that it realizes the at least one outlet opening region, for example, the hot air outlet opening region or at least shares in its realization or is a constituent part of the same.

The angle of incidence between the hot air stream and the substance air stream according to a preferred specific design is between 50 and 80° and in a preferred manner between 60 and 80°. A functionally reliable and targeted flowing away of the two air streams as one common substance hot air stream can be achieved at such an angle of incidence. Particularly good results are produced at an angle of around 70° and in an extremely preferred manner of between 68 and 72°.

With the at least one flow-guiding and/or deflecting device, the angle of incidence, in particular an angle of incidence as specified previously, between the hot air stream and the substance stream can be adjusted in a targeted manner such that the hot air stream and the substance air stream, when seen in the direction of flow and/or the direction of the vertical axis, meet one another at a defined height above the device at a defined impact point. If then, in this context, the at least one heating element heats the hot air stream to such a high temperature which drops to such a comparatively lower temperature at which eddying and/or turbulence occurs in the common substance hot air stream only at a defined distance above the impact point of the two air streams, the dispensing of the substance in space can then be influenced and adjusted in a targeted manner.

As already stated beforehand, a possible housing can be realized in a variety of ways, for example it can simply be formed by one single housing wall, for example by a plate-shaped housing wall. In a particularly preferred manner, however, the housing comprises multiple housing side walls and the housing forms preferably one more or less closed housing with a housing interior in which individual constituent parts of the device are received, shielded outwardly at least in regions toward the surrounding area (for example are also received in various chambers of the housing interior). In particular, in the case of such a design, the wick-side substance dispensing region preferably lies in a housing interior of the housing such that the substance air stream flows out of the housing interior via the substance outlet opening region toward the outside of the housing. In addition, at least the region of the at least one heating element assigned to the wick-side substance dispensing region lies in the housing interior, wherein it is provided, however, in a preferred manner that the region assigned to the wick-side substance dispensing region and also the region of the at least one heating element generating the substance-free hot air stream lie in the housing interior and as a result also the hot air stream flows out of the housing interior toward the outside of the housing. In order to ensure in particular in the latter case that the two air streams do not mix in the interior of the housing, the two regions are then spaced apart from one another in such a manner in the housing interior that the two air streams flow to the respective outlet opening region uninfluenced by one another and/or the two air streams are separated from one another, for example by means of a shielding element, such that they flow to the respective outlet opening region uninfluenced by one another.

According to a particularly preferred specific design, it is provided that at least one heating element serving for generating the hot air stream or, in the preferred event of one single heating element, a part region of the heating element serving for generating the hot air stream is assigned to the hot air outlet opening region, preferably is arranged directly adjacent to the hot air outlet opening region. This ensures in a simple manner that the hot air stream can flow away reliably via the hot air outlet opening region.

According to another particularly preferred specific design, it is provided that at least one heating element or in the event of one single heating element, a part region of the heating element is assigned to the wick-side substance dispensing region which, in turn, is assigned to the substance outlet opening region, preferably is arranged directly adjacent to the substance outlet opening region. Reliable flowing away of the substance air stream via the substance outlet opening region is possible as a result in a simple and functionally reliable manner.

The wick-side substance dispensing region is formed according to a particularly preferred design preferably by a free wick end which projects beyond a container, in particular a container opening, in such a manner that the heating element is assigned to the wick in the region of the free wick end. Such a design where the free wick end realizes the substance dispensing region enables a particularly simple assignment between the heating element and the wick.

According to a further particularly preferred specific design, the at least one heating element is an electrical heating element which comprises a heating body produced from a heat conducting material and at least one electrical resistance element, for example a PTC resistance element, which is thermally coupled with the heating body, is integrated and/or embedded (for example molded) preferably at least in part in the heating body and, for supplying power, is connectable to a power source and/or is suppliable with electrical power by means of a power source. Power is supplied, in this case, for example, via a line connection to an electrical connection element which, for example, can be formed by a plug or can comprise a plug, to name but one example. As an alternative to this, cable-free or contact-free power supply is also possible. Supplying power by means of a power pack, for example a battery arranged on the housing side, would also be possible in principle.

The heating body itself can be produced, for example, from a ceramic material that is a good conductor of heat or, however, also from a plastics material that is a good conductor of heat, to name but two examples.

The heating body comprises, in a preferred manner, a wick opening which is at a spacing from the electrical resistance element, that is to say is at a defined distance from the electrical resistance element, said wick opening being in the form of a through hole or, however, simply as an edge-side recess, into which the wick projects with the substance dispensing region, preferably with a free wick end which projects beyond the container, as substance dispensing region. The term "wick opening" is consequently to be understood explicitly here in a broad sense and includes all arrangement and assignment possibilities of a wick or of a free end of a wick with respect to a heat-emitting heat region or to a hole, recess, notch, opening or the like, whatever its form.

In particular in conjunction with such an electrical heating element, it is advantageous when a part region of the heating element, which serves for generating the hot air stream, is preferably assigned to the hot air outlet opening region and in an extremely preferred manner is arranged directly adjacent to the hot air outlet opening region, is formed by a hot air heating body region which, in particular for realizing a local hot spot on the heating body side, comprises the at least one or at least one electrical resistance element. With such a design, it is ensured in a simple manner in conjunction with the generation of the hot air stream that said hot air stream can flow away via the hot air outlet opening region in a functionally reliable manner.

For generating a particularly hot outflowing hot air stream, it can be provided, for example, that the at least one electrical resistance element is arranged in the region of a top side of the hot air heating body region, which is flowed around by the hot air stream and faces the hot air outlet opening region, preferably is integrated into the hot air heating body region in such a manner that the at least one electrical resistance element directly adjoins the top side of the hot air heating body region facing the hot air outlet opening region or realizes said top side in a shared manner.

In order to ensure that a relatively warm hot air stream is generated which comprises a particularly high flow speed and is correspondingly particularly advantageous for entraining the substance air stream enriched with substance to be dispensed, it is particularly advantageous when the local temperature maximum (hot spot) is realized on the part region of the heating element serving for generating the hot air stream, that is to say on the hot air heating body region, and a particularly good heat transfer to the air surrounding the hot air heating body region is also effected here.

To this end, it can be provided, for example, that the hot air heating body region of the heating body comprises a structure which enlarges the heat-dispensing surface.

As an alternative to this or in addition to it, the part region of the heating body which connects to the hot air heating body region and preferably comprises the wick opening can be realized such that no heat is dispensed or the heat dispensed to the surrounding area is reduced compared to the hot air heating body region and/or that a defined temperature gradient exists between said part region and the hot air heating body region with the temperature maximum in the hot air heating body region. With such measures, a targeted high level of heat emission is possible precisely where the hot air stream is to be realized, it also being possible in a reliable manner to avoid the two air streams being influenced reciprocally upstream of the outlet opening regions.

It can be provided specifically, for example, that the part region of the heating body which connects to the hot air heating body region and preferably comprises the wick opening is thermally insulated toward the outside at least in regions to avoid heat being emitted or to reduce the heat emitted compared to the hot air heating body region or is produced at least in regions, in particular at least in an outer edge region, from a material which comprises lower thermal conductivity than the material of the hot air heating body region.

It is further provided in a preferred manner that a part region of the heating element assigned to the wick-side substance dispensing region is formed by a wick heating body which comprises the wick opening.

In conjunction with an electrical heating element realized as described in more detail above, it is advantageous when the hot air heating body region generating the hot air stream and the wick heating body region comprising the wick opening (and consequently also the hot air outlet opening region assigned in each case thereto and the substance outlet opening region in the housing wall) are spaced apart from one another such that the two air streams flow to the respective outlet opening region uninfluenced by one another. With such a safety distance, it is ensured in a simple manner that the two air streams do not contact one another upstream of the outlet opening regions or in the interior of a/the housing, which would result in appearances of condensation or in unwanted turbulence.

In order to avoid reciprocal influence of the two air streams prior to their meeting, preferably upstream of the outlet opening regions or to keep them as small as possible, it can also be provided as an alternative to this or in addition to it that at least one shielding element is provided, by means of which the two air streams are separable from one another in the region upstream of the respective outlet opening regions. Said shielding element also forms in a preferred manner a constituent part of the flow guiding and/or deflecting device.

The shielding element can be realized, for example, on the housing side. Particularly preferred, as an alternative to this or in addition to it, is a functionally-integrated design where the heating element comprises and/or realizes the shielding element, preferably an upper part region of a heating body of the heating element facing the outlet opening regions. In this context, it can be provided specifically, for example, that the shielding element extends away from the heating element into the region of a recess of the housing wall and there realizes the substance outlet opening region and the hot air outlet opening region and/or separates them from one another at least in regions.

A further advantageous functional integration and consequently reduction in the number of components is produced with a design where an upper part region of the hot air heating body region facing the hot air outlet opening region is a constituent part of the flow-guiding and/or deflecting device and comprises and/or realizes a heating body-side flow-guiding element which guides and/or steers the hot air stream in the direction of the substance air stream, preferably comprises and/or realizes a heating body-side flow-guiding element which ascends in a ramp-shaped manner in the direction of the substance air stream and/or guides the hot air stream.

Quite preferred in this connection then is a design where the heating body-side flow-guiding element also realizes the shielding element at the same time.

According to a further particularly preferred embodiment which is also distinguished by advantageous functional integration, it can be provided that the heating body-side flow-guiding element together with a flow-guiding element assigned to the hot air outlet opening region, in particular a flow-guiding element as has already been appreciated previously, realizes the flow-guiding and/or deflecting device which guides and/or steers the hot air stream in the direction of the substance air stream.

The electrical resistance element can basically be any suitable resistance element, the use of a PTC resistance element, however, being preferred. PTC stands here for Positive Temperature Coefficient.

According to a further particularly preferred design, it is provided that the container is connectable to the housing, in particular releasably connectable. The container, in this case, can be insertable into the housing, in particular releasably insertable. This produces a compact and simply designed device overall.

The advantages produced with the method procedure correspond in an analogous manner to those of the device according to the invention so that, to avoid repetition, reference is made to the previously made statements.

The advantageous realizations and further developments of the invention explained above and/or reproduced in the subclaims can be used, in this case,—apart from, for example, in cases of clear dependencies or incompatible alternatives—individually or, however, also in arbitrary combinations with one another.

BRIEF DESCRIPTION OF THE SEVERAL VIEWS OF THE DRAWING

The invention and its advantageous realizations and further developments are explained in more detail below by way of simply exemplary and schematic drawings, in which.

DESCRIPTION OF THE INVENTION

Figure 1:
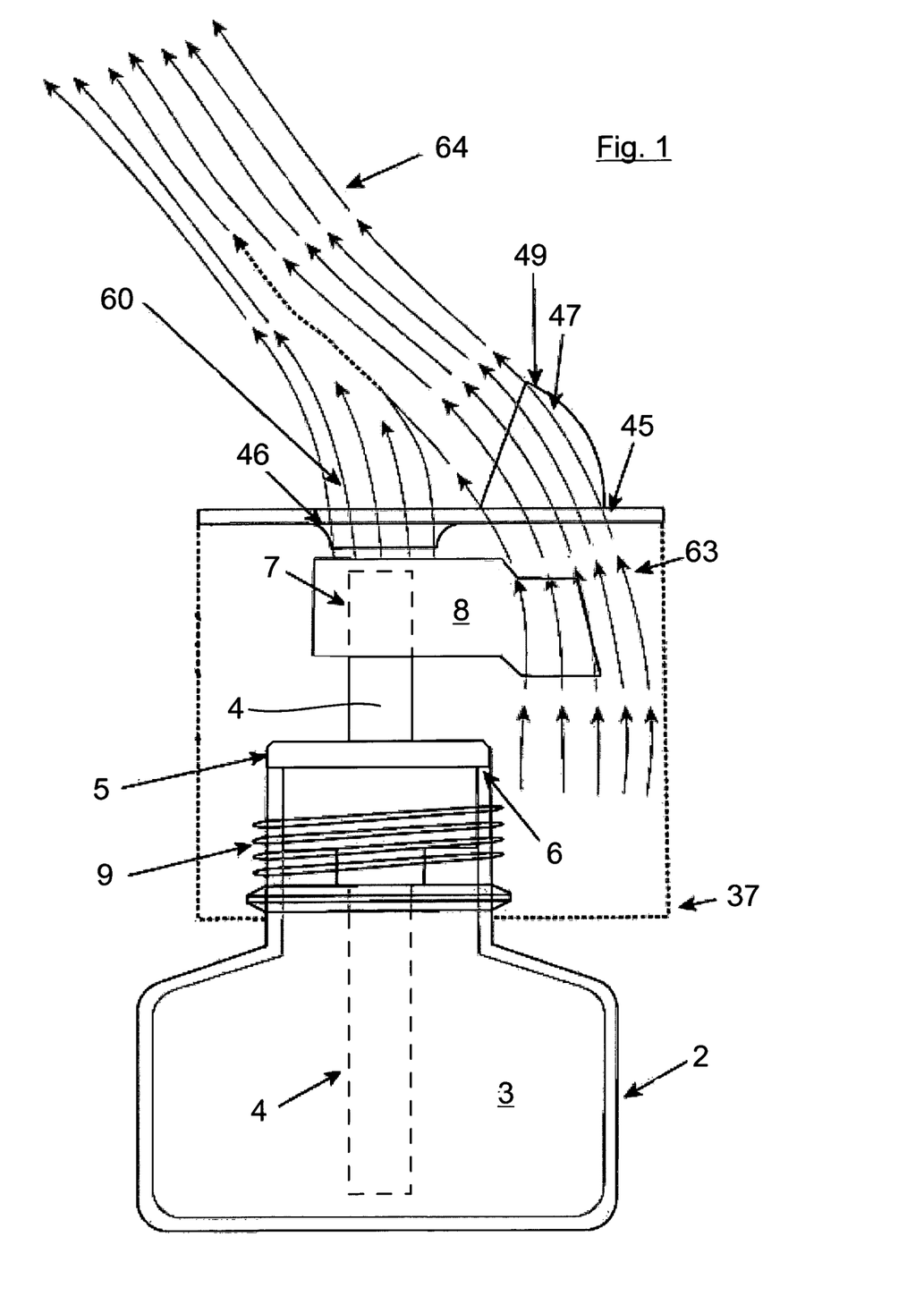
FIG. 1 shows a schematic representation of a schematic sketch of an exemplary embodiment according to the invention with a container, a wick arranged in the container projecting beyond the container by way of a free wick end and a heating element assigned to the free wick end.

FIG. 1 shows a schematic representation as an example of a schematic sketch of an exemplary embodiment of a device 1 according to the invention for dispensing, in particular for vaporizing, volatile substances, in particular fragrances and/or active agents. Said device 1 comprises a container 2 in which is received a substance 3 to be dispensed, for example in the form of a liquid.

Figure 2A:
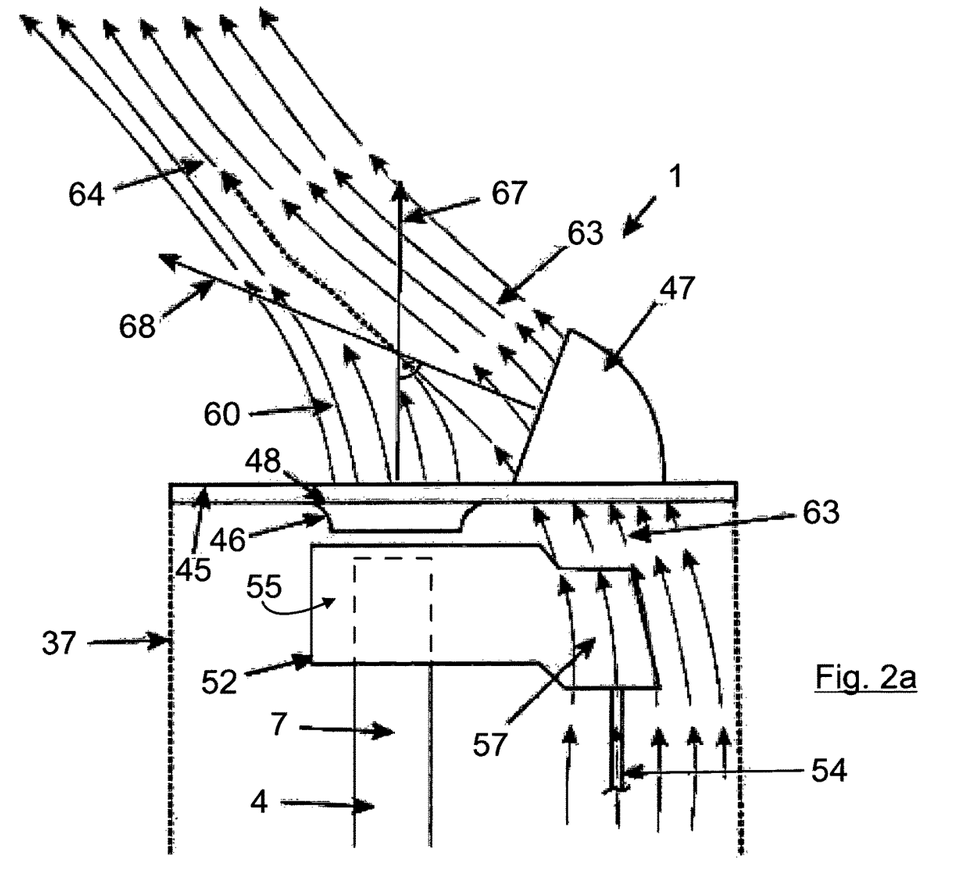
FIG. 2a shows a schematic representation of an enlarged schematic drawing of a detail of the air streams flowing away from the housing or the outlet opening regions thereof and meeting one another at a defined angle of incidence and realizing one common substance hot air stream.

A wick 4 as a capillary element is inserted into the container 2 and is in contact with the substance 3 to be dispensed, the wick 4 being inserted into a container opening 6 of the container 2 by means of a wick holder ring 5. Said wick holder ring 5 (see also FIG. 2) comprises a wick opening (not shown here) which surrounds the wick 4 in a bearing connection.

As can be seen further from FIG. 1, the wick 4 projects beyond the container or the container opening 6 with a free wick end 7 which realizes a substance dispensing region or a substance outlet surface, via which the substance conveyed upward into the region of the free wick end 7 on account of the capillary action of the wick 4 is output into the surrounding area.

To increase the dispensing rate, a heating element 8, which is described in more detail below and is in the form, for example, of an electrical heating element, is assigned to the free wick end 7, by means of which heating element the free wick end 7 is heatable to increase the dispensing or vaporizing rate.

The heating element 8 is a constituent part of a vaporizing device which is only shown extremely schematically in FIG. 1 and comprises a housing 37 which is only shown schematically, is sketched with a dotted line and into which the container 2 is insertable at least in regions, for example as shown in FIG. 1, can be screwed in by means of a thread 9. The substance can then escape or vaporize into the surrounding area as a substance air stream via a substance outlet opening, described in more detail below, in the housing 37.

FIG. 2*a* shows a schematic representation of an enlarged schematic drawing of the upper housing region of housing 37 together with an upper housing wall 45 which comprises the two adjacent outlet opening regions which are spaced apart from one another, one of which realizes a substance outlet opening region 46 and one a hot air outlet opening region 47.

Figure 4:
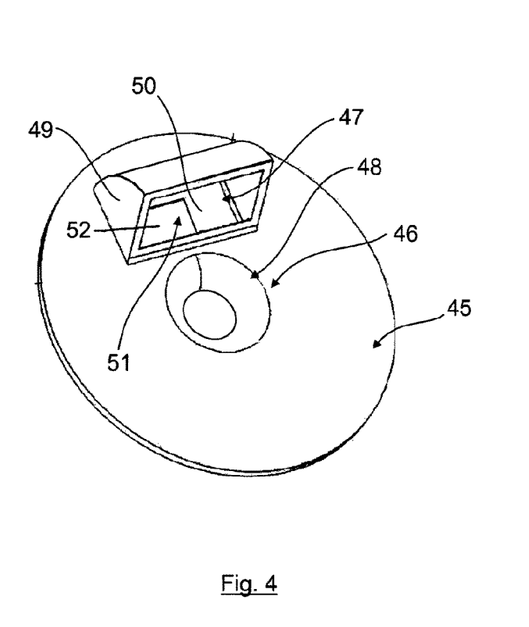
FIG. 4 shows a schematic representation of a perspective top view of the upper housing wall according to FIG. 2a and FIG. 5 shows a schematic representation of a cross section through the device in the region of the electrical heating element and in the region of the outlet opening regions.
Figure 5:
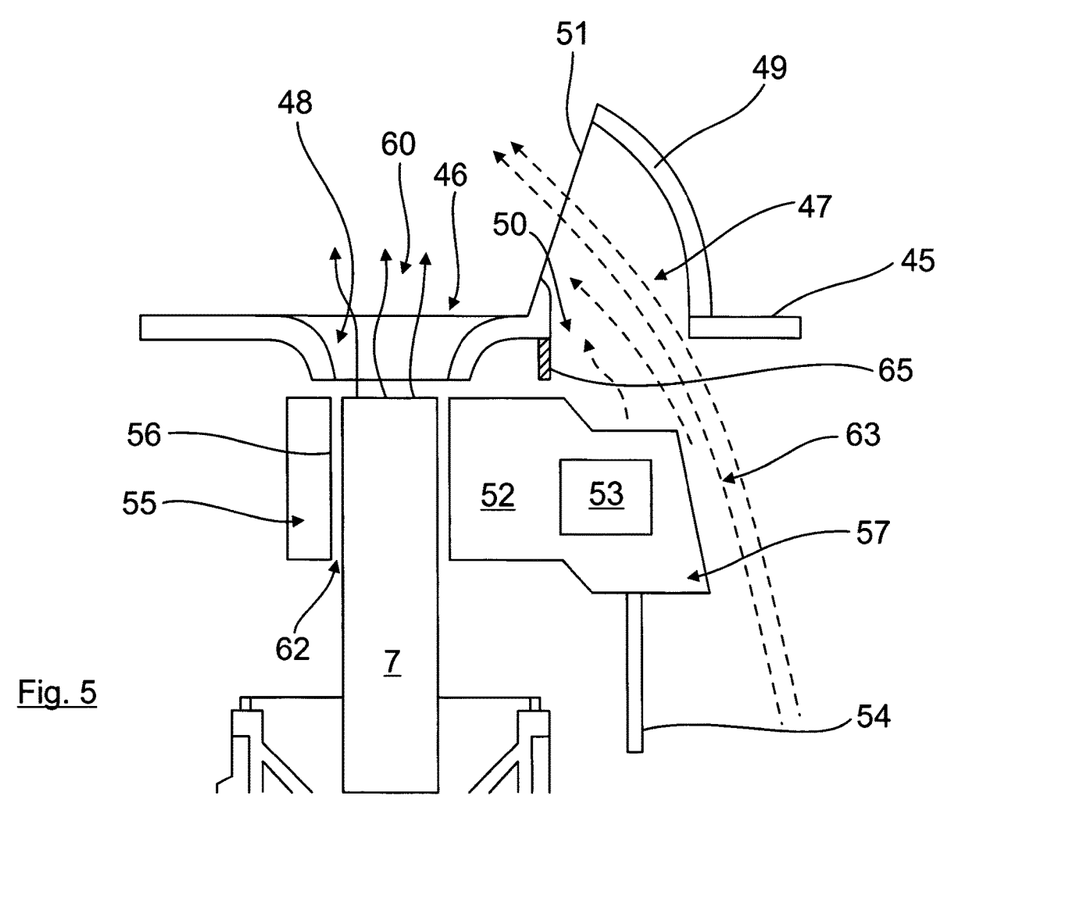

The substance outlet opening region 46, in this connection, is formed by a housing wall-side outlet opening 48, which can be seen in particular from the overall view of FIGS. 2*a*, 4 and 5. Said outlet opening 48 broadens, when seen in the direction of flow, here in a funnel-shaped manner as an example and with a convex curvature also an example.

Figure 2B:
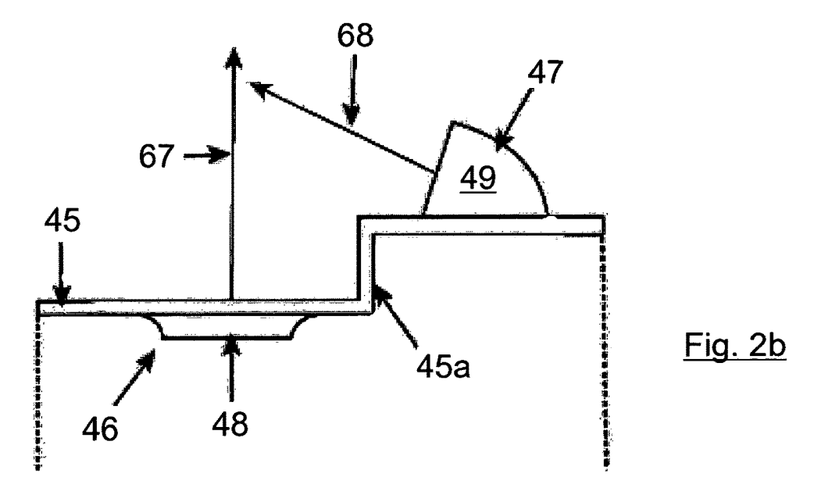
FIG. 2b shows a design of the upper housing wall as an alternative to FIG. 2a, FIG. 3 shows an enlarged representation of a perspective top view of a detail of the heating element.
Figure 3:
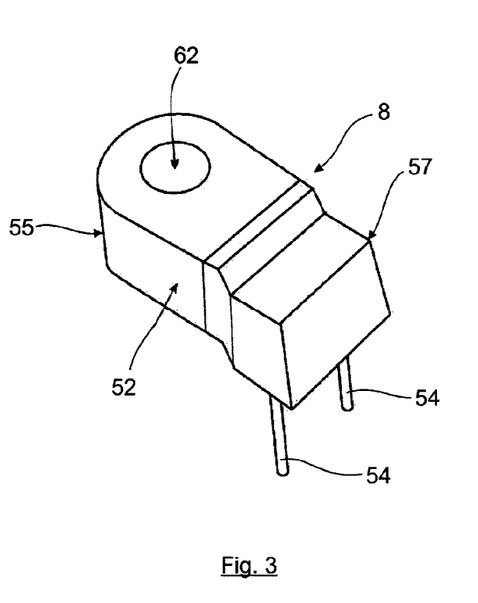

As can be seen further from FIGS. 2*a*, 4 and 5, the upper housing wall 45 is realized here in a planar or plate-shaped manner such that the substance outlet opening region 46 and the hot air outlet opening region 47, when seen in the direction of the vertical axis, lie side by side in one plane at a spacing and separated from one another by a wall region. As an alternative to this, the substance outlet opening region 46 and the hot air outlet opening region 47, when seen in the direction of the vertical axis, can, however, also lie side by side in different planes at a spacing and separated, as is shown schematically and as an example, for example, in FIG. 2*b*. The upper housing wall 45 is realized in a stepped manner here or comprises a stepped wall region 45*a*. Specifically here, the substance outlet opening region 46, when viewed in the direction of the vertical axis, is arranged below the hot air outlet opening region 47.

The hot air outlet opening region 47 also realizes here in a dual function the flow-guiding element of a flow-guiding and/or deflection device or realizes it in a shared manner and comprises a flow channel 49 which extends away from an inflow opening 50 (for example FIGS. 4 and 5), which is realized in the housing wall 45 and is curved, here as an example is hood-like. Said flow channel 49 is curved such that it realizes or comprises at its end opposite the inflow opening 50, an outflow opening 51 which points or is directed in the direction of the substance outlet opening region 46.

As can be seen further in FIGS. 2*a*, 4 and 5, the heating element 8, which comprises an elongated form here as an example, is arranged directly adjacent or below the two outlet opening regions 46, 47, which will now be described in more detail below:

the heating element 8 here is specifically an electrical heating element which comprises a heating body 52 produced from a heat conducting material and an electrical resistance element 53 which, as an example here, is embedded (for example molded) into the heating body 52. Said electrical resistance element 53 is connectable to a power source for supplying power, for example via contact lines 54 which are only shown schematically and in part here and are guided, for example, outside of the container 2 to an electrical connection element (not shown), which is formed, for example, by a plug or the like.

The heating body 52 comprises here a wick heating body region 55, in which a wick opening 56 is realized directly adjacent or below the outlet opening 48 of the substance outlet opening region 46. In said wick opening 56, the free wick end 7, realizing the substance dispensing region, is received at a defined gap clearance 62 from the opening wall, as can be seen in particular in FIG. 5, such that the free wick end 7, realizing the substance dispensing region, is also arranged directly adjacent or below the outlet opening 48 of the substance outlet opening region 46.

The heating body 52 comprises a further part region which connects to the wick heating body region 55 and realizes a hot air heating body region 57. The electrical resistance element 53 is arranged in said hot air heating body region 57, said hot air heating body region 57 together with the electrical resistance element 53 received therein being arranged directly adjacent or below the inflow opening 50 of the hot air outlet opening region 47.

In a preferred manner, the hot air heating body region 57 realizes a local heating body-side hot spot.

To this end, the wick heating body region 55 connecting to the hot air heating body region 57 can be realized such that no heat is dispensed or the heat dispensed to the surrounding area is reduced compared to the hot air heating body region 57 and/or that a defined temperature gradient exists between the wick heating body region 55 and the hot air heating body region with the temperature maximum in the hot air heating body region 57. In order to achieve this, it can be provided, for example, that the part region of the heating body 52 which connects to the hot air heating body region 57 and is formed substantially by the wick heating body region 55, is thermally insulated toward the outside at least in regions to avoid heat being emitted or to reduce the heat emission compared to the hot air heating body region 57 or is produced at least in regions, in particular at least in an outer edge, from a material which comprises lower thermal conductivity than the material of the hot air heating body region 57.

Even if the heating body 52 is realized in a stepped manner here, any other forms can obviously also be used, in particular non-stepped forms.

As a result of heating the free wick end 7 or the tip of the free wick end 7, particularly effective vaporization of the substance to be dispensed accumulating in the free wick end 7 is obtained, which results in a clear increase in the rates of vaporization.

The free wick end 7 is preferably received with a gap clearance 62 in the wick opening 56.

The substance air stream 60 generated in this manner then flows via the outlet opening 48 through the upper housing wall 45 to outside the housing 37.

The electrical resistance element 53 in the hot air heating body region 57 is preferably a PTC resistance element.

As a result of the hot air heating body region 57 being arranged directly below the hot air outlet opening region 47, heat is emitted to the air surrounding the hot air heating body region 57, as a result of which, a substantially substance-free hot air stream 63 is generated which is considerably hotter than the substance air stream 60 and, as a result, also comprises a considerably higher speed than the substance air stream 60.

Said hot air stream 63 then flows via the inflow opening 50 into the curved flow channel 49 and is then deflected on account of the curvature of the flow channel 49, which realizes a flow-guiding element or a flow-guiding and/or deflecting device, such that said hot air stream 63 meets the substance air stream 60 at a defined angle of incidence $\alpha$ (compare FIG. 1, FIG. 2*a* and FIG. 5) and entrains it thereby realizing one common substance hot air stream 64 which flows away from the device 1, as a result of which the substance to be dispensed is distributed in space in a considerably more effective manner.

As can be seen in particular in FIG. 2*a*, the substance air stream 60 flowing away from the substance outlet opening region 46 or the outlet opening 48 is an air stream which is uninfluenced, is aligned in a substantially rectilinear manner (see flow arrow 67) and flows away from the substance outlet opening region 46 or the outlet opening 48, which substance air stream the hot air stream 63, deflected by means of the flow channel 49, meets at a defined angle of incidence α.

The angle of incidence α between the hot air stream 63 and the substance air stream 60 is, for example, between 50 and 80°, in a preferred manner between 60 and 80° and in an extremely preferred manner approximately 70°, the angle of incidence α being measured here between the flow arrows 67 and 68 which define the main direction of flow of the two air streams 60 and 63.

In order to ensure that the substance air stream 60 and the hot air stream 63 do not interact in the region upstream or below the respective outlet opening regions 46, 47 or in the interior of the housing 37, it can be provided that the hot air heating body 57 and the wick heating body region 55, which comprises the wick opening 56, are at a certain minimum distance from one another. As an alternative to this or in addition to it, as is shown only schematically in FIG. 5, it is also possible, where applicable, to provide an additional shielding element 65, for example a wall-like shielding element, by means of which the two air streams 60, 63 are separated from one another in a functionally reliable manner in the region upstream or below the respective outlet opening regions 46, 47. Said shielding element 65 can also extend even further downward and, for example, realize an inside wall, through which the heating body 52 is guided such that the two heating body regions 55, 57 lie on different sides of the inside wall as a shielding element.

With such a concept, the efficiency of substance dispensing in space or the efficiency of the vaporizing can be improved considerably.

Figure 6:
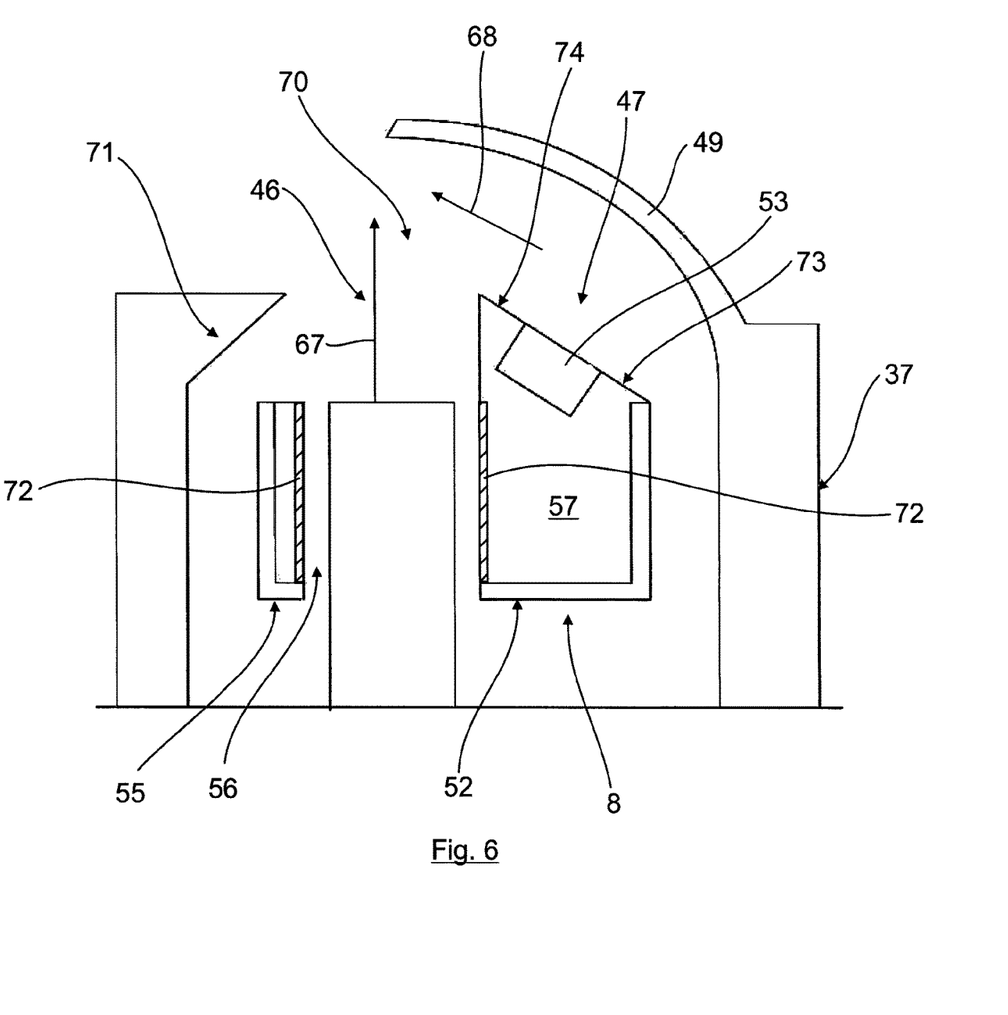
FIG. 6 shows an alternative and particularly advantageous design of a device according to the invention and FIG. 7 shows as an example by way of the embodiment according to FIG. 6, a schematic sketch representing the flow conditions in the region above the device.

FIG. 6 shows an alternative and particularly advantageous design of a device 1 according to the invention, functionally identical components being designated with identical reference symbols.

Specifically here, the substance outlet opening region 46 is a constituent part of a housing wall-side recess 70 which also realizes or comprises the hot air outlet opening region 47 at the same time, such that the substance outlet opening region 46 and the hot air outlet opening region 47 are realized or arranged directly adjacent or adjoining one another in the upper housing wall 45.

As is shown schematically in FIG. 6, the recess region, which realizes or is assigned to the substance outlet opening region 46, is tapered upward in the direction flow of the substance air stream (tapering region 71) in order to enable a defined output of the substance air stream 60 via the substance outlet opening region 46.

Here too, the heating body 52 of the electrical heating element 8 (analogously to the first embodiment described previously) once again comprises a wick heating body region 55 in which a wick opening 56 is realized directly adjacent or below the substance outlet opening region 46. In said wick opening 56, the free wick end 7, realizing the substance dispensing region, is received with a defined gap clearance 62 from the opening wall such that the free wick end 7, realizing the substance dispensing region, is also arranged directly adjacent or below the substance outlet opening region 46.

A ring produced from a heat conductive material, preferably of an aluminum, is inserted in the wick opening, only as an example here, said ring serving for the purpose of moderating the temperature in the region of the wick opening 56 or helps to avoid local hot spots in the region of the wick opening such that the free wick end 57 is heated uniformly on all sides in the wick opening. Such a ring 72 can obviously also be used in the case of the first embodiment described previously, that is to say in general in conjunction with wick openings and is not bound to the embodiment according to FIG. 6.

The heating body 52 further comprises here too, once again, a further part region which connects to the wick heating body region 55 and realizes a hot air heating body region 57. The electrical resistance element 53 is arranged in said hot air heating body region 57, said hot air heating body region 57 together with the electrical resistance element 53 received therein being arranged directly adjacent or below the hot air outlet opening region 47.

Specifically here, the electrical resistance element 53 is only arranged as an example in the region of a top side 73 of the hot air heating body region 57 facing the hot air outlet opening region 47, preferably is integrated in such a manner into the hot air heating body region 57 that the electrical resistance element 53 directly adjoins the top side of the hot air heating body region 57 facing the hot air outlet opening region 47 or even realizes said top side in a shared manner.

The upper part region 74 of the hot air heating body region 57 comprising the top side 73 and facing the hot air outlet opening region 47 realizes here, at the same time, a constituent part of the flow-guiding and/or deflecting device and realizes a heating body-side flow-guiding element which ascends in a ramp-shaped manner in the direction of the substance air stream (characterized by the flow arrow 67) and guides the hot air stream (characterized by the flow arrow 68).

As can be seen very well additionally in FIG. 6, the ramp-shaped flow-guiding element, which is realized by the upper part region 74, extends here toward the mouth opening region of the recess 70 or into the mouth region of the recess 70 until it also realizes, at the same time, a shielding element which separates the substance air stream and the hot air stream in the region upstream of the housing wall or in the interior of the housing 37 from one another in a functionally reliable manner and at the same time also realizes the substance outlet opening region 46 and the hot air outlet opening region 47 in a shared manner or separates them more or less from one another.

The heating body-side flow-guiding element, formed by the upper part region 74, together with the flow-guiding element 49 which is assigned to the hot air outlet opening region 47, (which can be formed here, for example, simply by a guide vane or, however, can also be a constituent part of a flow channel or of a flow hood, as has been described previously) realizes the flow-guiding and/or deflecting device which guides and/or steers the hot air stream 63 in the direction of the substance air stream 60.

Figure 7:
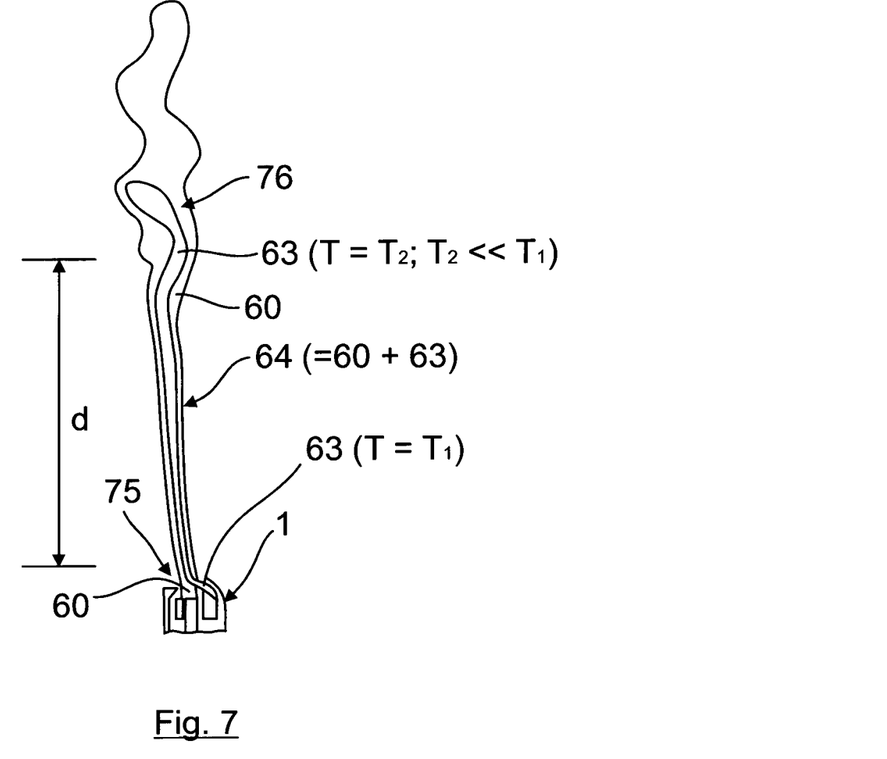

FIG. 7 then shows as an example, by way of the embodiment according to FIG. 6, the flow conditions in the region above the device 1. The same applies substantially analogously to the embodiment in FIGS. 1 to 5.

If the hot air stream 63 is deflected by means of the flow-guiding element 49 such that it meets the substance air stream 60 at an angle of incidence α, as specified previously, the hot air stream 63 and the substance air stream 60, when seen in the direction of flow and/or of the vertical axis, then meet one another at a defined height above the device 1 at an impact point 75 and realize one common substance hot air stream 64. If the heating element 8 then heats the hot air stream 63 in this context to such a high temperature, which only drops to such a temperature at which eddying and/or turbulence 76 occurs in the common substance hot air stream 64 at a defined distance d above the impact point 75 of the two air streams, this is precisely the point in said region that the substance is dispensed in space in a targeted manner such that it is possible to influence and adjust the vaporizing in a targeted manner.

This is shown schematically in FIG. 7 such that the hot air stream 63 comprises a temperature T1 in the region of the device 1, whilst the hot air stream 63 as a constituent part of the substance hot air stream 64 comprises a temperature T2, which is clearly lower than the temperature T1, at a distance d from the impact point 75.

The invention claimed is:

1. A device for dispensing volatile substances, the device comprising:
   a container for a substance to be dispensed;
   a wick as a capillary element which is in contact with the substance to be dispensed, is at least partly disposed in the container, forms a constituent part of the container and includes a wick-side substance dispensing region;
   at least one heating element configured to generate a substance air stream, which is enriched with the substance and flows away from the device, by emitting heat to said wick-side substance dispensing region and to generate a substantially substance-free hot air stream, which flows away from the device by emitting heat to air surrounding said at least one heating element; and
   at least one of a flow guide or a deflector configured to at least one of guide or deflect at least one of the substance or substance-free hot air streams, such that the substance and substance-free hot air streams flowing away from the device meet one another and realize a common substance hot air stream flowing away from the device.

2. The device according to claim 1, further comprising a housing having a housing wall formed with a substance outlet opening region and wherein:
   said wick-side substance dispensing region is assigned to said substance outlet opening region in said housing wall;
   the substance air stream flows away from the device in said substance outlet opening region;
   said housing wall is formed with at least one further outlet opening region being a hot air outlet opening region, via which the hot air stream flows away from the device, such that the air streams flowing away from the substance outlet opening region and from the hot air outlet opening region meet one another in a region outside said housing and realize the common substance hot air stream which flows away from the device.

3. The device according to claim 2, wherein said flow guide or said deflector includes at least one flow-guiding element which is assigned to at least one of the substance air stream or to the substance outlet opening region, at least one which is assigned to the substance-free hot air stream or to the hot air stream outlet opening region by means of which an air stream flowing away from the device is guidable or deflectable in the direction of the other air stream.

4. The device according to claim 2, wherein said substance outlet opening region and said hot air outlet opening region, when viewed in a direction of a vertical axis, at least one of lie side by side substantially in one vertical plane or adjoin one another, such that said housing wall, at least in a housing wall region including the substance outlet opening region and the hot air outlet opening region, is realized in at least one of a planar or plate-shaped manner, or in that the substance outlet opening region and the hot air outlet opening region, when viewed in the direction of the vertical axis, lie side by side spaced apart on different levels, such that the hot air outlet opening region, when viewed in the direction of the vertical axis, lies above the substance outlet opening region.

5. The device according to claim 2, wherein:

the substance air stream flowing away from the substance outlet opening region is an air stream which flows away from the substance outlet opening region in an uninfluenced manner; and at least one flow-guiding element of the flow guide or the deflector is assigned to the hot air outlet opening region, by which the hot air stream flowing away from the hot air outlet opening region is deflectable so that the hot air stream meets the substance air stream in an angular manner or at a defined angle of incidence.

6. The device according to claim 5, wherein said substance outlet opening region is formed by a housing wall-side outlet opening that broadens outwardly in a funnel shape in a direction of flow, and wherein the hot air outlet opening region comprises a separate housing wall-side opening that is separated from said outlet opening by a wall.

7. The device according to claim 5, wherein said substance outlet opening region is a constituent part of a housing wall-side opening which also forms said hot air outlet opening region.

8. The device according to claim 2, wherein:

the wick-side substance dispensing region lies in a housing interior of said housing such that the substance air stream flows out of the housing interior via the substance outlet opening region outside said housing; and at least the region of said at least one heating element assigned to said wick-side substance dispensing region lies in the housing interior, the region assigned to the wick-side substance dispensing region and the region of the at least one heating element generating the substance-free hot air stream lie in the housing interior and the hot air stream also flows out of the housing interior outside the housing, wherein the two regions are at least one of arranged or are spaced apart from one another in the housing interior such that the substance and substance-free hot air streams flow to the respective outlet opening region uninfluenced by one another or wherein the substance and substance-free hot air streams are separated from one another such that the substance and substance-free hot air streams flow to the respective outlet opening region uninfluenced by one another.

9. The device according to claim 2, wherein a part region of the heating element serving for generating the substance-free hot air stream is assigned to the hot air outlet opening region.

10. The device according to claim 2, wherein a part region of the heating element is assigned to said wick-side substance dispensing region which, in turn, is assigned to said substance outlet opening region.

11. The device according to claim 3, wherein said flow-guiding element is aligned in a direction of the other air stream.

12. The device according to claim 3, wherein said flow-guiding element extends from at least one of said substance outlet opening region or said hot air outlet opening region away to the outside, away from said housing wall.

13. The device according to claim 12, wherein said flow-guiding element is a guide vane or a flue or channel which, when seen in the direction of flow, extends away from an inflow opening, wherein at an end thereof opposite the inflow opening, the flow shaft or channel comprises an outflow opening which points in the direction of the other air stream.

14. The device according to claim 3, wherein said flow-guiding element forms said at least one further outlet opening region or is a constituent part thereof.

15. The device according to claim 1, wherein an angle of incidence between the hot air stream and the substance air stream lies between 50 and 80 degrees.

16. The device according to claim 1, wherein:
at least one of the flow guide or the deflector at least one of predefines or adjusts an angle of incidence between the hot air stream and the substance air stream such that the hot air stream and the substance air stream, when seen in at least one of the direction of flow or the direction of a vertical axis, meet one another at a defined height above the device at an impact point; or
said at least one heating element heats the hot air stream to a temperature which drops to a temperature at which at least one of eddying or turbulence occurs in the substance hot air stream at a defined distance above the impact point of the two air streams.

17. The device according to claim 1, wherein said wick-side substance dispensing region is formed by a free wick end projects beyond a container such that said heating element is assigned to said wick in a region of said free wick end.

18. The device according to claim 1, wherein said at least one heating element is an electrical heating element which comprises a heating body produced from a heat conducting material, and at least one electrical resistance element which is thermally coupled with said heating body, is at least one of integrated or embedded at least in part in said heating body and said heating body is to be supplied with electrical power from a power source.

19. The device according to claim 18, wherein said heating body is formed with a wick opening into which the wick with the substance dispensing region projects.

20. The device according to claim 18, wherein a partial region of said heating element which serves for generating the hot air stream is assigned to said hot air outlet opening region and is arranged directly adjacent said hot air outlet opening region, is formed by a hot air heating body region which, for realizing a local hot spot on a heating body side, includes at least one electrical resistance element.

21. The device according to claim 20, wherein said at least one electrical resistance element is arranged at a top side of said hot air heating body region facing from the hot air outlet opening region, in such a manner that said at least one electrical resistance element directly adjoins the top side of said hot air heating body region facing the hot air outlet opening region or realizes said top side in a shared manner.

22. The device according to claim 20, wherein said hot air heating body region of said heating body comprises a structure which enlarges a heat-emitting surface thereof.

23. The device according to claim 20, wherein a part region of said heating body, which connects to said hot air heating body region and is formed with a wick opening, is realized such that no heat is emitted or the heat emitted to the surrounding area is reduced compared to at least one of the hot air heating body region or in that a defined temperature gradient exists between said part region and the hot air heating body region with a temperature maximum in said hot air heating body region.

24. The device according to claim 23, wherein the part region of said heating body which connects to said hot air heating body region is thermally insulated toward the outside at least in regions to avoid heat being emitted or to reduce the heat emitted compared to said hot air heating body region or is produced at least in regions from a material having a lower thermal conductivity than a material of said hot air heating body region.

25. The device according to claim 23, wherein a part region of said heating element which is assigned to said wick-side substance dispensing region is formed by a wick heating body region which comprises the wick opening.

26. The device according to claim 25, wherein said hot air heating body region generating the hot air stream and said wick heating body region including said wick opening are spaced apart from one another such that the substance and substance-free hot air streams flow to the respective said outlet opening region uninfluenced by one another.

27. The device according to claim 20, wherein an upper part region of said hot air heating body region facing said hot air outlet opening region is a constituent part of said flow guide or said deflector and includes a heating body-side flow guiding element which at least one of guides or steers the hot air stream in a direction of said substance air stream.

28. The device according to claim 27, wherein said heating body-side flow-guiding element is configured as a shielding element.

29. The device according to claim 27, wherein said heating body-side flow-guiding element together with a flow-guiding element assigned to said hot air outlet opening region at least one of realizes said flow guide or said deflector which at least one of guides or steers the hot air stream in a direction of the substance air stream.

30. The device according to claim 1, further comprising at least one shielding element for separating the two air streams from one another prior to the meeting thereof, such that the substance and substance-free hot air streams flow to the respective said outlet opening region uninfluenced by one another.

31. The device according to claim 30, wherein said shielding element is at least one of a constituent part of a housing or said heating element includes said shielding element.

32. The device according to claim 31, wherein said shielding element extends away from said heating element into the region of a recess of a housing wall of said housing and there at least one of realizes said substance outlet opening region and said hot air outlet opening region or separates them from one another at least in regions.

33. The device according to claim 1, wherein said container is releasably connectable to a housing such that said container is insertable into said housing.

34. A method for dispensing volatile substances with a device, the method comprising:
providing a container containing a substance to be dispensed and having a wick forming a capillary element in contact with the substance to be dispensed, the wick being arranged at least in regions in the container, forming a constituent part of the container and having a wick-side substance dispensing region;
heating the wick-side substance dispensing region with at least one heating element for generating a substance air stream that is enriched with substance and flows away from the device;

heating air surrounding the at least one heating element for generating a substantially substance-free hot air stream that flows away from the device and is warmer than the substance air stream;

at least one of guiding or deflecting at least one of the substance or substance-free hot air streams with at least one flow guide or deflector, such that the substance and substance-free hot air streams flowing away from the device meet one another and form one common substance hot air stream that flows away from the device.

35. The method according to claim 34, which comprises:

at least one of:

defining an angle of incidence between the hot air stream and the substance air stream by the at least one flow guide or deflector, such that the hot air stream and the substance air stream, when seen in at least one of the direction of flow or a direction of a vertical axis, meet one another at a defined height above the device at an impact point, or heating the hot air stream with the at least one heating element to a temperature which drops to a temperature at which at least one of eddying or turbulence occurs in the substance hot air stream only at a defined distance above the impact point of the two air streams.

* * * * *